US012721606B2

(12) United States Patent
Sandrin et al.

(10) Patent No.: US 12,721,606 B2
(45) Date of Patent: Sep. 1, 2026

(54) ELASTOGRAPHY DEVICE AND METHOD

(71) Applicant: ECHOSENS, Paris (FR)

(72) Inventors: Laurent Sandrin, Bourg-la-Reine (FR); Stéphane Audière, Paris (FR); Véronique Miette, L'Hay-les-Roses (FR)

(73) Assignee: ECHOSENS SA, Paris (FR)

( * ) Notice: Subject to any disclaimer, the term of this patent is extended or adjusted under 35 U.S.C. 154(b) by 0 days.

(21) Appl. No.: 18/767,484

(22) Filed: Jul. 9, 2024

(65) Prior Publication Data

US 2026/0013837 A1 Jan. 15, 2026

(51) Int. Cl.
*A61B 8/00* (2006.01)

(52) U.S. Cl.
CPC .............. *A61B 8/543* (2013.01); *A61B 8/485* (2013.01)

(58) Field of Classification Search
CPC ................................ A61B 8/543; A61B 8/485
See application file for complete search history.

(56) References Cited

U.S. PATENT DOCUMENTS 10,459,043 B2 * 10/2019 Vahala ................. G01R 33/285
2011/0301468 A1 * 12/2011 Sandrin ................ A61B 5/6843 73/575
2013/0150704 A1 * 6/2013 Vitek .................. A61B 5/4538 600/411
2015/0032000 A1 * 1/2015 Park ....................... A61B 8/485 600/438
2016/0174945 A1 * 6/2016 Oh ....................... A61B 8/4405 382/131
2016/0213341 A1 * 7/2016 Salcudean ................ A61B 6/50
2019/0076084 A1 * 3/2019 Kanegae .............. A61B 5/4812
2019/0192119 A1 * 6/2019 Salcudean ............ A61B 8/4227
2020/0390421 A1 * 12/2020 Audière .................. A61B 8/14
2021/0137634 A1 * 5/2021 Lang ...................... A61B 90/00
2021/0196235 A1 * 7/2021 Bae ........................ A61B 8/585
2021/0205561 A1 * 7/2021 Eger .................... A61B 5/0803
2022/0386987 A1 * 12/2022 Camps ................. A61B 5/0205
2023/0264049 A1 * 8/2023 Zachs ................. A61B 8/4209 600/439
2023/0293154 A1 9/2023 Audière et al.

(Continued)

FOREIGN PATENT DOCUMENTS

EP 4 245 224 A1 9/2023

OTHER PUBLICATIONS

Anders, M et al., "Rapid MR elastography of the liver for subsecond stiffness sampling," International Society for Magnetic Resonance in Medicine, Aug. 2023, pp. 312-324.

(Continued)

*Primary Examiner* — Dixomara Vargas
(74) *Attorney, Agent, or Firm* — CUSHMAN PARTNERS, LLC

(57) ABSTRACT

An elastography method implemented by an elastography device, the method including obtaining a respiratory signal related to a respiratory activity of a subject; and acquiring a plurality of measurements of a mechanical property of a region of a body of the subject, the region being a part of a liver or a spleen of the subject, wherein each measurement among at least a subset of the plurality of measurements of the mechanical property is acquired at a same moment of a respective respiratory cycle determined from the respiratory signal.

20 Claims, 7 Drawing Sheets

(56) References Cited

U.S. PATENT DOCUMENTS

2024/0225606 A1* 7/2024 Sandrin ................ A61B 8/5223
2024/0382177 A1* 11/2024 Sandrin .................. A61B 8/543

OTHER PUBLICATIONS

Byenfeldt, M., et al., "Influence of Probe Pressure on Ultrasound-Based Shear Wave Elastography of the Liver Using Comb-Push 2-D Technology," Ultrasound in Medicine and Biology, vol. 45, Issue 2, (Year: 2018), pp. 411-428.
Millonig, G., et al., "Liver stiffness is directly influenced by central venous pressure," Journal of Hepatology, vol. 52, No. 2, Feb. 2010, pp. 206-210.
Dhillon, J. K., et al., "Use of liver stiffness measurements in acute decompensated heart failure: new applications of a non-invasive technique," ESC Heart Failure, Jul. 12, 2022, 8 pages.
Kobalava, Z., et al., "Prognostic Value of Admission-to-Discharge Change in Integral Congestion Assessment for Predicting Adverse Outcomes in Patients with Decompensated Heart Failure," Archives of Razi Institute, vol. 77, No. 3, Jun. 2022, pp. 1049-1058.
Extended European Search Report as issued in European Patent Application No. 24306150.4, dated Nov. 21, 2024.
Ling, W., et al., "Assessment of impact factors on shear wave based liver stiffness measurement," European Journal of Radiology., vol. 82, No. 2, Feb. 2013, pp. 335-341, XP093223416.

* cited by examiner

ELASTOGRAPHY DEVICE AND METHOD

FIELD

The present invention relates to the field of elastography, for example liver or spleen elastography. More specifically, the invention relates to an elastography device and an elastography method to accurately determine a measurement of the liver stiffness or the spleen stiffness of a subject.

BACKGROUND

Measuring liver stiffness (LS) has been shown to be a very useful tool to help health care professionals detect or characterize liver disease or damages, and more generally monitor the condition of the liver of a subject.

There are basically two kinds of elastography techniques for measuring stiffness: strain imaging and shear wave imaging. In strain imaging, a normal stress is applied to the tissue and the normal strain is measured. The Young's modulus is then determined from the applied normal stress and the measured normal strain. In shear wave imaging, a dynamic stress is applied to the tissue and shear waves created by the excitation are then followed to derive a measurement of the stiffness of the tissue. Techniques based on shear wave imaging include Point Shear Wave Elastography (pSWE), 2D Shear Wave Elastography (SWE) and 1D Transient Elastography (TE). An example of 1D Transient Elastography is the Vibration-Controlled Transient Elastography (VCTE) used in the FibroScan® system.

The VCTE-based elastography devices typically provide several measurements of the stiffness of the tissue (for example the liver or the spleen) collected at different time-points when the operator triggers measurements (for example by pressing a button to generate a transient displacement). A unique value representative of the stiffness measurement is then derived from these measurements (for example, the final measurement may be a mean or a median of the series of measurements. To obtain a reliable measurement of liver stiffness, it is generally recommended to obtain a series of 10 stiffness measurements.

Even if this technology works well and provides very satisfying results, it is known that variability in the series of stiffness measurements can be quite large.

There are many factors that can influence the stiffness value of certain organs, such as the liver or the spleen, and which can therefore induce variability in the stiffness measurements. For example, liver stiffness measurements (LSM) or spleen stiffness measurements (SSM) are influenced by central venous pressure and more generally by hemodynamics effects, as detailed in the article "Liver Stiffness Is Directly Influenced by Central Venous Pressure" by G. Millonig et al., Journal of Hepatology, volume 52, Issue 2, February 2010, pp. 206-210.

SUMMARY

The inventors of the present invention investigated whether other factors could explain this variability, and how such factors might be considered in the evaluation of the liver stiffness or spleen stiffness of the subject, for example to assess liver fibrosis or portal hypertension, respectively.

An aspect of the invention relates to an elastography method in which the acquisition of measurements is synchronized to particular moments of the subject's breathing.

An aspect of the invention therefore relates to an elastography method implemented by an elastography device, the method comprising:

obtaining, using a respiratory sensor, a respiratory signal related to a respiratory activity of a subject; and acquiring, using an elastography probe of an elastography device, a plurality of measurements of a mechanical property of a region of a body of the subject, the region being a part of a liver or a spleen of the subject;

wherein each measurement among at least a subset of the plurality of measurements of the mechanical property is acquired at a same moment of a respective respiratory cycle determined from the respiratory signal.

By "mechanical property", it is meant any physical property or parameter relating to the behavior of the region of the human body when subjected to one or more mechanical stresses. For example, the mechanical property may be conventional quantities such as stiffness, elasticity, Young's modulus, shear modulus, shear wave speed, viscoelasticity, viscosity, ultrasound attenuation, speed of sound, backscatter coefficient (BSC), etc. The mechanical property may also be any value derived from one or more of these physical properties or parameters.

In the following, particular reference is made to stiffness, but aspects of the invention apply to other mechanical properties. Also, particular reference is made to the liver as a region of the body, but aspects of the invention could apply to the spleen.

By "respiratory signal", it is meant a set of data relating to a respiratory activity of the subject. In particular, this data set may include information indicating when the subject is inhaling, exhaling, and the start and end times of inhalations or expirations.

In the examples described below, the respiratory signal corresponds to a signal representing the temporal variations in the volume of the subject's chest, acquired using a respiratory belt. It will be appreciated that the invention is not limited to such a signal. For example, the respiratory signal may be acquired by an air sensor located near the subject's nose or mouth, or by a microphone analyzing noises near the subject's nose or mouth to determine whether the subject is breathing in or out. The different sensors (air sensor, microphone, . . . ) described herein to acquire the respiratory signal can be broadly termed respiratory sensors.

By "measurements acquired at a same moment of a respiratory cycle", it is meant measurements acquired at different respiratory cycles, at similar moments or instants in time (e.g. a specific time or time period) in the different respiratory cycles. For example, the measurements may all be acquired at the end of an expiration period.

It is understood that the moments are determined based on the respiratory signal. For example, when the respiratory signal is a signal representing the chest's diameter of the subject, the end of an inspiration may correspond to a local maximum in the respiratory signal, and an end of an expiration may correspond to a local minimum in the respiratory signal. When the respiratory signal corresponds to information provided by an air sensor, the end of an expiration corresponds to the moment when there is no more outgoing air detected at the exit of the nose and/or the mouth.

By "each measurement among at least a subset of the plurality of measurements of the mechanical property is acquired at a same moment", it is meant that not all measurements are necessarily taken at the same time in the respiratory cycle. For example, it is possible to take several measurements during the same respiratory cycle. In this case, there is a first subset of measurements taken at the same first instant of the respiratory cycle, a second subset of measurements taken at the same second instant of the respiratory cycle, a third subset of measurements taken at the same third moment of the respiratory cycle, etc. For example, a couple measurements can be acquired per respiratory cycle: one measurement at the end of the inspiration and one measurement at the end of the expiration. Therefore, the plurality of measurements comprises a subset of measurements acquired at the end of the inspiration and a subset of measurements acquired at the end of the expiration.

As detailed hereinafter, the inventors have in fact determined that there is variability in the measurements of the mechanical property which is due to the breathing of the subject. This variability is greatly reduced when the measurements are acquired at the same time of the respiratory cycle.

Furthermore, depending on the point in the respiratory cycle at which the measurements are taken, different properties of the examined body part can be inferred. For example, measurements taken at the end of an expiration are much more correlated with fibrosis, while measurements taken at the end of an inspiration are more representative of a cardiovascular state. Thus, the moments can be chosen according to the diagnostic information targeted.

A benefit of the elastography method according to an aspect of the invention is an improvement in the precision of the measured values, and therefore in the diagnostic quality of these values. Another benefit is that the elastography method according to an aspect of the invention does not require the subject to hold their breath (it is even desirable that the subject breathes normally during the procedure), which can be very uncomfortable or very complicated, particularly for subjects with obesity problems or respiratory pathologies.

In one or more embodiments, each measurement of the plurality of measurements of the mechanical property may be acquired at a same moment of a respective respiratory cycle determined from the respiratory signal.

In other words, in these embodiments, all the measurements are taken in different respiratory cycles (i.e. there is at most one measurement per respiratory cycle), and at similar moments of their respective respiratory cycles (for example, at the end of the expiration).

In one or more embodiments, the plurality of measurements of the mechanical property may be partitioned into a plurality of subsets of measurements, each subset of measurements comprising measurements acquired at a respective moment of the respiratory cycle, the moments of the respiratory cycle associated with different subsets of measurements being different from each other.

In these embodiments, several measurements are taken during the same respiratory cycle, at respective specific times. Thus, the plurality of measurements comprises a first subset of measurements taken at similar first moments of their respective respiratory cycles (for example at the end of inspiration) and a second subset of measurements taken at similar second moments of their respective respiratory cycles. respective respiratory cycles (for example at the end of expiration).

In one or more embodiments, the method may further comprise, for each measurement of the plurality of measurements:

- detecting an event in the respiratory signal, the event corresponding to a beginning of an inspiration, an end of an inspiration, a beginning of an expiration, or an end of an expiration, and
- acquiring the measurement upon the detection of the event It is understood that in the case where there are several measurements per respiratory cycle, the measurements of the same respiratory cycle can be acquired upon detection of respective events, which may or may not be the same.

For example, each measurement of the plurality of measurement may be acquired at a respective time corresponding to a time at which the corresponding event related to the cardiac signal is detected.

In these embodiments, the acquisitions of measurements are synchronized with the detection of the corresponding events.

Alternatively, each measurement of the plurality of measurement may be acquired at a respective time corresponding to a time at which the corresponding event related to the cardiac signal is detected delayed by a predefined temporal offset.

In these embodiments, the acquisitions of measurements are delayed compared to the detection of the corresponding events.

In one or more embodiments, the method may further comprise: determining, from the plurality of measurements, a feature related to the mechanical property.

As mentioned above, acquiring the measurements at same moment(s) of the respiratory cycle reduces the variability between the measurements and therefore increases the accuracy of the evaluation of a feature relating to the mechanical property from the acquired measurements.

For example, the feature may be a function of a maximum, a minimum, a mean, a standard deviation and/or a percentile of the measurements.

In one or more embodiments, the feature may further be function of at least one value of the respiratory signal.

Another aspect of the invention relates to an elastography system comprising an elastography probe and an electronic unit configured to:

- receive a respiratory signal related to a respiratory activity of a subject; and
- acquire a plurality of measurements of a mechanical property of a region of a body of the subject, the region being a part of a liver or a spleen of the subject;
- wherein each measurement among at least a subset of the plurality of measurements of the mechanical property is acquired at a same moment of a respective respiratory cycle determined from the respiratory signal.

It is noted that aspects of the present invention may be implemented as part of any elastography technique.

For example, the above method may be implemented in the context of Transient Elastography techniques, including ARFI (Acoustic Radiation Force Impulse), SWE (Shear Wave Elastography), TE (Transient Elastography) or VCTE (Vibration-Controlled Transient Elastography). Therefore, in one or several embodiments, the elastography device may comprise:

- a probe that comprises: a protruding part to be applied against the body of the subject and at least one ultrasound transducer;

wherein, for determining each of the measurements of the mechanical property, the electronic unit may be adapted to:

- deliver to the body of the subject, via the protruding part, a transient, low frequency mechanical pulse;

upon delivery of said mechanical pulse, control the ultrasound transducer to emit a sequence of ultrasound pulses, and acquire echo signals received in response by the ultrasound transducer to track how a low frequency elastic wave induced by the mechanical pulse propagates through the region of the body of the subject;

determine the respective measurement of the mechanical property related to low frequency elastic wave propagation.

In particular, the elastography device may be a VCTE device. In this case, the probe may further comprise a low frequency vibrator arranged to move the protruding part of the probe, and the delivery of the transient, low frequency mechanical pulse may comprise:

control, by the electronic unit, the low frequency vibrator to deliver to the body of the subject said transient, low frequency mechanical pulse.

By "transient pulse", it is meant a mechanical vibration that is temporary. The duration of the pulse, that is the active time, during which there is a substantial motion protruding part (induced by the vibrator in the case of a VCTE device) is followed by a downtime during which there is no or substantially no motion of the protruding part. By substantially no motion, it is meant for instance that, during this downtime, the displacement of the protruding part that may be induced by the vibrator remains smaller than 1/10 or even 1/20 of the peak displacement of protruding part. For the transient pulses mentioned above, an actuation ratio, equal to the pulse's active time, divided by the sum of this active time and the following down time, is typically below 50%, or even below 20%. The downtime is the duration between the end of the active time and a subsequent significant motion of the protruding part (corresponding for instance to a subsequent transient, mechanical pulse), should there be any.

By low frequency pulse, it is meant that the central frequency of the pulse is below 500 Hz, or even below 250 Hz and for example greater than 20 Hz. The central frequency of the pulse is, for instance, the average or the median frequency of the spectrum of the displacement or of the speed of displacement corresponding to that pulse, or the peak frequency of a main peak of this spectrum, or the mean of the −3 dB, −6 dB or −20 dB cutoff frequencies of the spectrum.

In one or more embodiments, when the elastography device is a VCTE device, a peak-to-peak amplitude of a displacement of the protruding part of the probe induced by the low frequency vibrator may be between 0.2 and 10.0 mm, for example between 0.5 and 3.0 mm.

Yet another aspect of the invention relates to an elastography system comprising an elastography device as defined above and a respiratory device configured to acquire the respiratory signal.

The respiratory device may use any technique to obtain the respiratory signal. Also, it is understood that the respiratory device may be external to the elastography device or may be part of the elastography device.

Yet another aspect of the invention relates to a non-transitory computer readable storage medium, having stored thereon a computer program comprising program instructions, the computer program being loadable into a data-processing unit and adapted to cause the data-processing unit to carry out the steps of the elastography method when the computer program is run by the data-processing device.

Other features and benefits of the method and apparatus disclosed herein will become apparent from the following description of non-limiting embodiments, with reference to the appended drawings.

BRIEF DESCRIPTION OF THE DRAWINGS

Aspects of the present invention are illustrated by way of example, and not by way of limitation, in the figures of the accompanying drawings, in which like reference numerals refer to similar elements and in which.

DETAILED DESCRIPTION

One or more aspects of the invention pertains to an elastography method and device constructed and arranged to provide accurate measurements regardless of variables that have an impact on the measurement, such as operator experience, patient respiration, or blood pressure.

The inventors of the present invention have investigated the influence of respiration on the values of liver stiffness measurement (LSM) or spleen stiffness measurements (SSM).

During the respiratory cycle, abdominal pressure varies. This variation is even greater in the case of abdominal breathing (also called diaphragmatic breathing, as opposed to thoracic breathing). These variations induce changes in the LSM or SSM measurements. To better understand these changes, the inventors simultaneously measured both LSM and respiratory signals.

Figure 1:
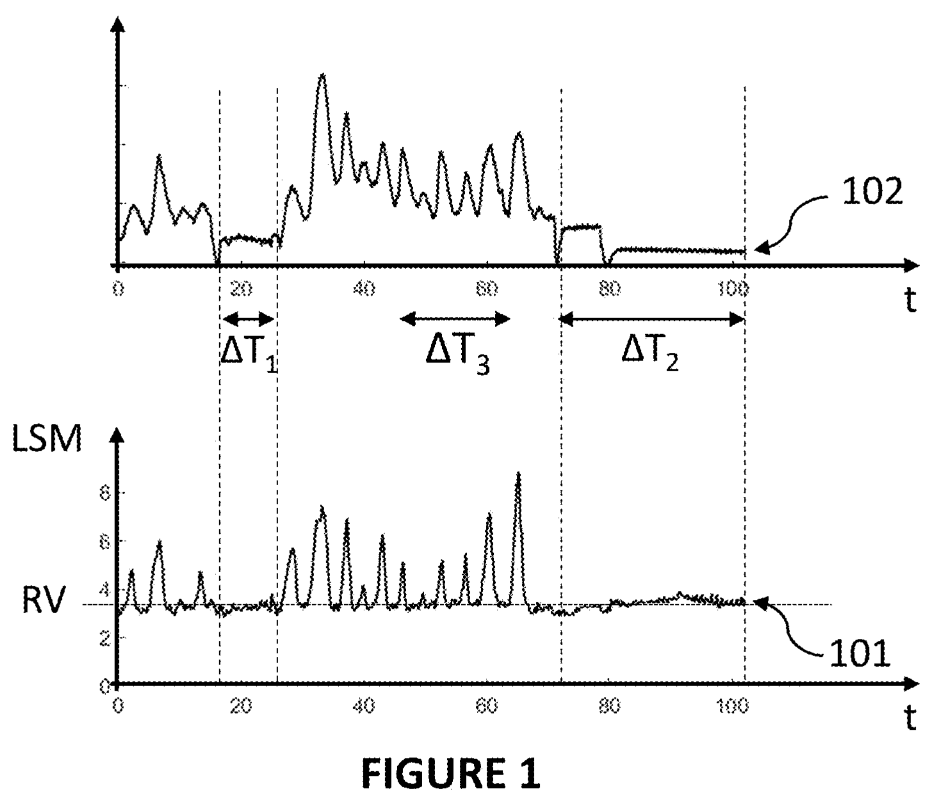
FIG. 1 represents the variations of an LSM signal and a respiratory signal over time.

FIG. 1 illustrates the results obtained on one subject. In particular, FIG. 1 represents two curves:

a curve 101 representing the LSM signal; and a curve 102 representing the respiratory signal.

The LSM signal 101 was acquired using a VCTE elastography device configured to acquire several liver stiffness measurements per minute, similar to the device presented in patent application EP22305298.6 assigned to the applicant of the present patent application.

Indeed, given that the respiratory frequency of an adult is of the order of 12 to 20 cycles per minute, which means one cycle every 3 to 5 seconds, each cycle being composed of one inspiration and one expiration (in which inspiration occupies approximately one third of the respiratory cycle, and the expiration occupies approximately two thirds of the respiratory cycle), it was interesting to acquire measurements at a sufficiently high rate (at least 4 measurements per second, for example 10 measurements per second) to follow more precisely the variations of the LSM over time, and in particular during a respiratory cycle. The LSM signal 101 is expressed in Kilopascals (kPa).

The respiratory signal 102 was acquired by a respiratory belt measuring changes in chest diameter over time. This signal 102, whose amplitude depends on the subject's chest diameter, is expressed in arbitrary units. To maximize the correlation between the measurement signal 101 and the respiratory signal 102, the respiratory belt can be placed close to the region in which the mechanical property is measured.

It is understood that all the observations deduced from these curves also apply to a spleen stiffness measurement (SSM) signal. Indeed, it is known that the LSM and the SSM are correlated, and that variations in the LSM values are repercussed in the SSM values. Thus, the variations observed in the LSM signal linked to hemodynamic changes and changes in abdominal pressure are also observable in the SSM signal. Therefore, aspects of the present invention also applies to an SSM signal.

Referring back to FIG. 1, it first appears from the curves 101, 102 in FIG. 1 that LSM values increase during inspiration (i.e. when the respiratory signal 102 is increasing) and decrease during expiration (i.e. when the respiratory signal 102 is decreasing). Thus, the peaks of the LSM signal 101 coincide temporally with the peaks of the respiratory signal 102.

In addition, the value of the peaks (i.e. local maxima) of the LSM signal 101 depends on the volume of inspired air (the "deeper" the inspiration, the higher the value of the LSM peak), while the minimum values of the LSM signal 101 (at the end of respiratory cycle or at the start of respiratory cycle) remains relatively stable.

The relative stability of the minimum values of the LSM signal 101 is all the more remarkable since these minimum values are not affected by the minimum values of the respiratory signal 102. This can be shown in FIG. 1, which represents two time intervals $\Delta T_1$, $\Delta T_2$ during which the subject voluntarily held his breath. The first time interval $\Delta T_1$ (around 20-25 seconds) is associated with a first average value of the respiratory signal 102. The second time interval $\Delta T_2$ (around 70-100 s) is associated with a second average value of the respiratory signal 102 lower than the first value (i.e. the average value of the respiratory signal 102 over time interval $\Delta T_1$). It is noted that the "gap" observed in the respiratory signal 102 during the second time interval $\Delta T_2$ (around 80 s) may be caused by a movement of the respiratory belt, or by the fact that the belt has been tightened.

Two observations can be made:

- the temporal variations of the LSM signal 101 are lower during periods of apnea $\Delta T_1$, $\Delta T_2$ (the peaks are lower than when the subject is breathing); and
- the average value of the LSM signal 101 is approximately the same over the two periods of apnea $\Delta T_1$, $\Delta T_2$, and approximately corresponds to the values of the LSM signal at the end or start of a respiratory cycle.

FIG. 1 also represents a third time interval $\Delta T_3$ (around 40-55 s) during which the subject is breathing: the respiration curve 102 presents rises and falls corresponding respectively to inspirations and expirations. During this third time interval $\Delta T_3$, the values of local minimums vary quite significantly. In contrast, over this same time interval, the values of the local minimums of the respiratory signal 102 vary very little.

Generally speaking, it can be observed that the minimum values of the LSM signal 102 vary relatively little around an average value RV (represented in FIG. 1), independently of variations in the values of the respiratory signal 101. Conversely, the maximum values (i.e. the upward peaks) of the LSM signal 102 vary significantly, and in a manner correlated with the respiratory signal 101.

It is noted that other factors than respiration can generate variations in the LSM signal, for example hemodynamic effects. Indeed, in the not yet published patent application EP24305031.7 assigned to the same applicant, the inventors noticed that variations in the cardiac signal (in particular the components of the CVP waveform) can be observed in the LSM signal.

From these observations, the inventors of the present invention arrived at the following conclusion: as the liver stiffness measurement (LSM) signal fluctuates in sync with the respiratory cycle, it is beneficial to acquire liver stiffness measurements at specific points during respiration (for example, taking a measurement at the beginning of each inhalation). Such synchronization of the acquisition of liver stiffness (LS) measurements makes it possible to reduce the variability of the measurements. Indeed, it appears from FIG. 1 that if the measurements are acquired at the same moments of the different respiratory cycles, their variability is much lower than if these measurements are carried out randomly, as it is conventionally done with existing elastography devices (in which case, a measurement can correspond to a high peak, another at a low peak, another at a median value, etc. and the variability of these measurements can thus become very high).

It is noted that an alternative would be to calculate the different measurements when the subject is in apnea. However, this involves unpleasant constraints for the subject (who must hold his breath several times). Additionally, depending on when the subject holds their breath (for example, at the end of an inspiration or at the end of an expiration), the average values of the respiratory signal during apnea periods are different, as are the values of the abdominal pressure. This may have an impact on the measurement of LS (and therefore generate variability in the measurements, which reduces their diagnostic value).

An aspect of the present invention can beneficially be carried out while the subject is breathing, thus making the examination less unpleasant for the subject, and allowing a more precise evaluation of the measurement.

In one or more embodiments, a single measurement is acquired during a respiratory cycle, and all measurements are acquired at the same time of their respective respiratory cycle. For example, each measurement may be acquired at the beginning or the end of an inspiration, or at the beginning or the end of an expiration.

It is noted that on the curve of the respiratory signal 102 in FIG. 1, an inspiration corresponds to an ascending portion of the curve 102, and an expiration corresponds to a descending portion of the curve 102. Therefore, the acquisition of the measurement may be triggered upon detection of an upward peak (when the measurement is acquired at an end of an inspiration or the beginning of an expiration) or a downward peak (when the measurement is acquired at an end of an expiration or the beginning of an inspiration) in curve of the respiratory signal 102.

Figure 2A:
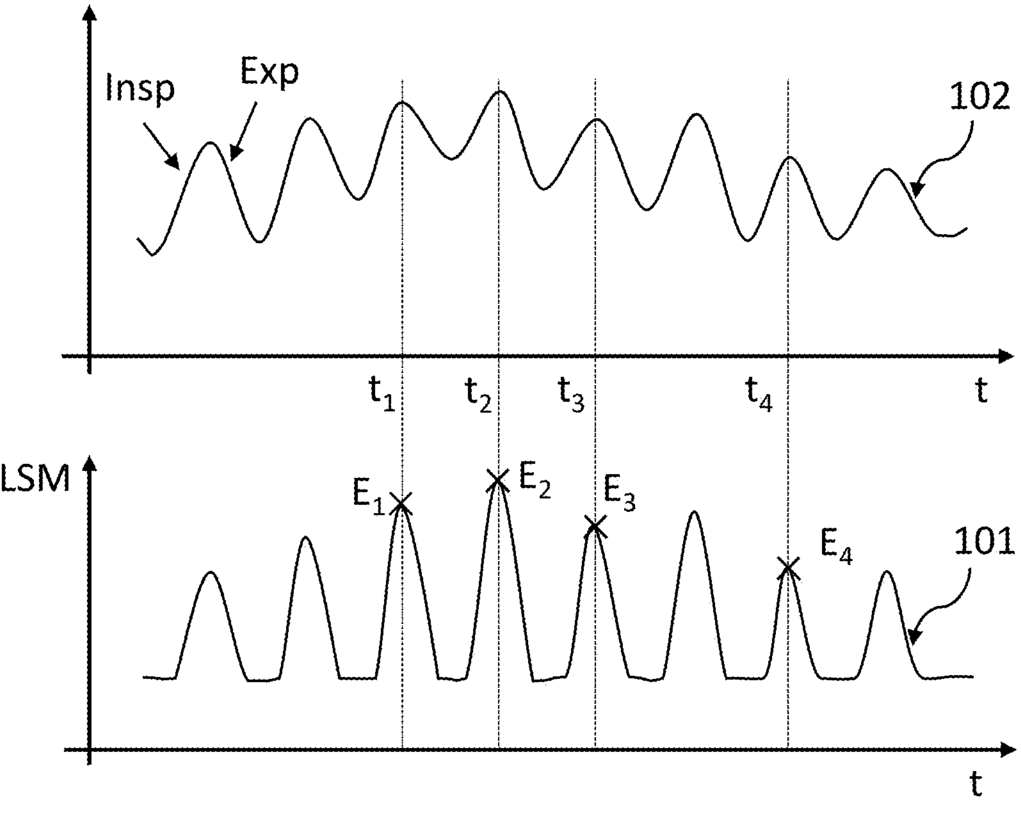
FIGS. 2*a*, 2*b* and 2*c* illustrate several embodiments for acquiring measurements upon detection of specific moments in the respiratory signal.
Figure 2B:
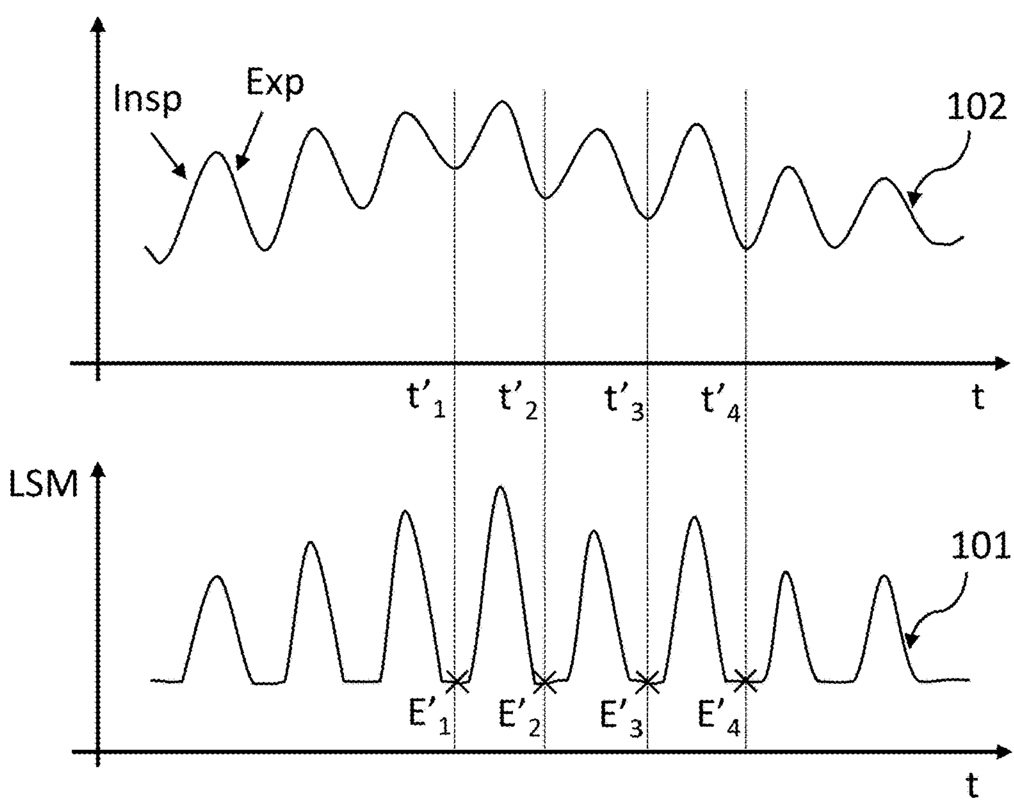

Such embodiments are represented in FIGS. 2*a* and 2*b*. FIGS. 2*a* and 2*b* represent a schematic, simplified version of the curves 101, 102 of FIG. 1. As in FIG. 1, curve 101 represents the LSM time signal, and curve 102 represents the respiratory time signal.

As mentioned above, a phase during which the respiratory signal 102 is increasing corresponds to an inspiration ("Insp" in FIGS. 2*a* and 2*b*) and a phase during which the respiratory signal 102 is decreasing corresponds to an expiration ("Exp" in FIGS. 2*a* and 2*b*).

In the example of FIG. 2*a*, the measurements $E_1$, $E_2$, $E_3$, $E_4$ are acquired at different times $t_1$, $t_2$, $t_3$, $t_4$ corresponding to ends of inspiration (or, approximately equivalently at times corresponding to beginnings of expiration). In this example, the detection of an upward peak (i.e. a local maximum) in the curve of the respiratory signal 102 therefore triggers the acquisition of a corresponding LS measurement $E_1$, $E_2$, $E_3$, $E_4$.

In some embodiments, a measurement is acquired at each upward peak in the respiratory signal 102. However, this is not mandatory, and it is possible that at certain upward peaks, no measurement is acquired—this is particularly the case in the example shown in FIG. 2*a*, in which no measurement is taken during of the intermediate peak between times $t_3$ and $t_4$. For example, it is possible that at certain peaks in the respiratory signal, the elastography device is not ready to acquire a measurement.

In the example of FIG. 2*b*, the measurements $E'_1$, $E'_2$, $E'_3$, $E'_4$ are acquired at different times $t'_1$, $t'_2$, $t'_3$, $t'_4$ corresponding to beginnings of inspiration (or, approximately equivalently at times corresponding to ends of expiration). In this example, the detection of a downward peak (i.e. a local minimum) in the curve of the respiratory signal 102 therefore triggers the acquisition of a corresponding LS measurement $E'_1$, $E'_2$, $E'_3$, $E'_4$.

In some embodiments, a measurement is acquired at each downward peak in the respiratory signal 102. However, this is not mandatory, and it is possible that at certain downward peaks, no measurement is acquired.

The detection of an upward or downward peak in a signal is known and is not further detailed here. For example, an upward or downward peak may be detected by detecting that a rising or a falling edge of the signal reaches a predefined threshold.

It is noted that the acquisition of a measurement may be carried out at times other than at the end or the beginning of an expiration or an inspiration. For example, it is possible to acquire the measurement at the expiration of a predefined time offset following a peak (upward or downward).

Also, it is noted that in embodiments, derived measurements can be calculated from the acquired LS measurements and the corresponding respiratory signal values. For example, a derived measurement can be equal to $E_i/V_i$, where Vi corresponds to the value of the respiratory signal at the time the measurement $E_i$ is acquired, or $E_i/V$, where V is an average value of the respiratory signal over a time window associated with measurement $E_i$, etc.

In alternative embodiments, several measurements may be acquired during a same respiratory signal. For example, two measurements may be acquired during one respiratory cycle: one measurement acquired at the end of the expiration (or the beginning of the inspiration) of the respiratory cycle, and one measurement acquired at the end of the inspiration (or the beginning of the expiration) of the respiratory cycle.

Figure 2C:
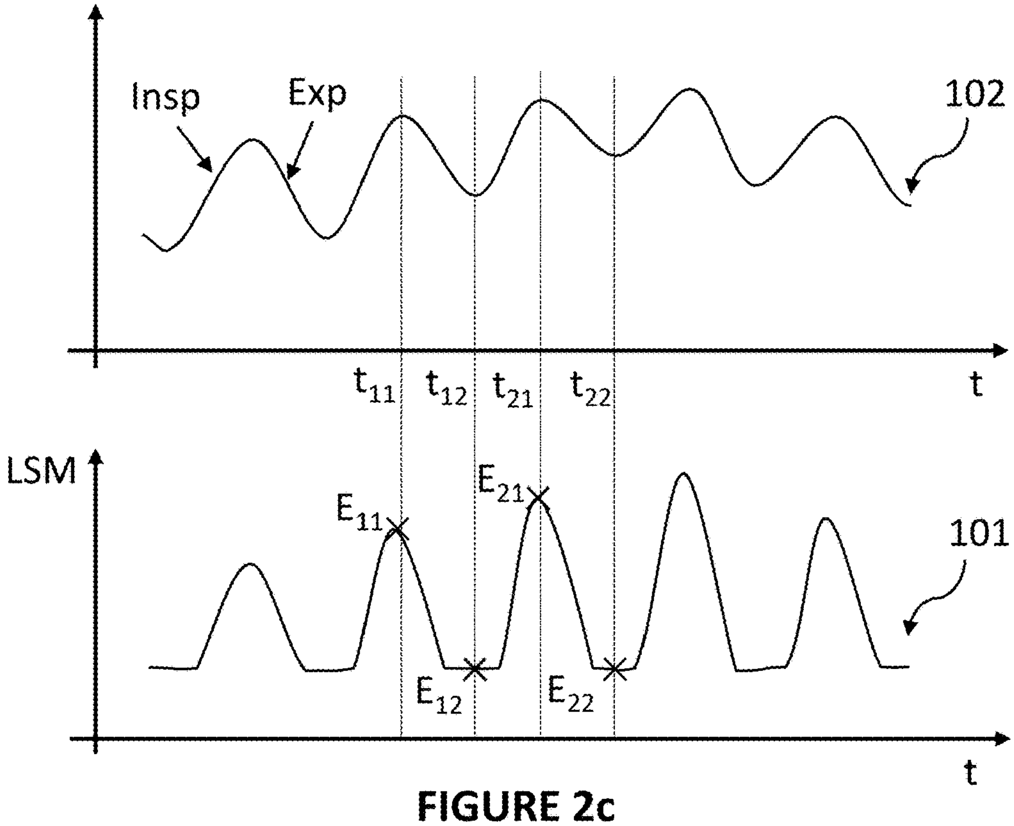

Such embodiment is represented in FIG. 2*c*. In the example of FIG. 2*b*, the measurements $E_{11}$, $E_{12}$, $E_{21}$, $E_{22}$ are acquired at different times $t_{11}$, $t_{12}$, $t_{21}$, $t_{22}$. $E_{11}$ and $E_{21}$ are acquired at respective times $t_{11}$ and $t_{21}$ corresponding to two successive ends of inspiration (or, approximately equivalently, at two successive beginnings of expiration). $E_{12}$ and $E_{22}$ are acquired at respective times $t_{12}$ and $t_{22}$ corresponding to two successive beginning of inspiration (or, approximately equivalently, at two successive ends of expiration).

It is thus possible to obtain estimations of the amplitude (i.e. the difference between the maximum value and the minimum value) of the LSM signal over several respiratory cycles. For example, these measurements may then be used to determine a value representative of the amplitude of the LSM signal. In the example of FIG. 2*c*, two estimations of the amplitude are obtained: $a_1=E_{11}-E_{12}$ and $a_2=E_{21}-E_{22}$. It will be appreciated that the number of estimates (i.e. the number of respiratory cycles during which measurements are acquired) can be greater than 2, for example around five, ten or even more than ten. It is then possible to calculate, for example, the average, or a percentile of all the estimates obtained, to have a single value representative of the amplitude of the LSM signal 101.

Instead of using values of the LS measurements themselves, it is possible to use normalized values, taking into account the values of the respiratory signal when acquiring the measurements. For example, if $V_{ij}$ denotes the value of the respiratory signal 102 at the time the measurement $E_{ij}$ is acquired, the estimations above may be replaced by:

$$a_1 = E_{11}/V_{11} - E_{12}/V_{12} \text{ and } a_2 = E_{21}/V_{21} - E_{22}/V_{22}$$

or:

$$a_1 = (E_{11} - E_{12})/(V_{11} - V_{11}) \text{ and } a_2 = (E_{21} - E_{22})/(V_{21} - V_{22})$$

or another function of $E_{11}$, $E_{12}$, $E_{21}$, $E_{22}$, $V_{11}$, $V_{12}$, $V_{21}$ and $V_{22}$.

It will be appreciated that depending on the desired information and the medical application envisaged, it is possible to acquire either a single measurement during a respiratory cycle (always at the same moment of the cardiac cycle), or several measurements during the same respiratory cycle.

Indeed, referring again to FIG. 1, the observed curves 101, 102 indicate that the upward peaks in the LSM signal 101 are mostly influenced by abdominal pressure, while local minima (or the low plateaus) of the LSM signal 101 are probably more correlated with stiffness of the parenchyma (and therefore with a level of fibrosis).

To go further, this means that the LSM signal can be seen as the combination of two components:

- a "dynamic" component reflecting the influence of pressure variations inside the part of the body for which the stiffness is measured and of respiration on the signal; and
- a "resting" component, which is not influenced by these factors, and in particular by respiration. This resting component reflects the more static contribution from the liver parenchyma and is believed to be much more linked to the fibrosis than the dynamic component. This resting component typically corresponds to a component of the signal around the value RV in FIG. 1.

Furthermore, it has be observed that, when the probe is inclined relative to a position perpendicular to the surface of the subject's body where it is applied, the measurement thus acquired is generally higher than the true value of the measurement. Thus, a lack of perpendicularity of the probe in relation to the subject's body leads to overestimates of the measurement value. The resting component also eliminates or reduces overestimations related to probe perpendicularity.

Thus, the dynamic component of the signal reflects variations due to respiration as well as the effect of blood pressure due to hemodynamic and cardiovascular characteristics, while the resting component is mainly correlated to fibrosis.

Therefore, if the LS measurements are used as part of the diagnosis of fibrosis, it may be interesting to trigger the acquisition of each measurement at a low peak of the LSM signal, i.e. at the end of expiration (or at the start of inspiration). This corresponds to the example of FIG. 2*a*.

If the LS measurements are used as part of the diagnosis of a cardiovascular affection it may be interesting to trigger the acquisition of each measurement at a high peak of the LSM signal, i.e. at the beginning of expiration (or at the end of inspiration). This corresponds to the example of FIG. 2*b*.

If the aim is to evaluate the hemodynamic and cardiovascular variations, it may be interesting to acquire, for a plurality of respiratory cycles, two measurements: one measurement at the high peak of the LSM signal and one measurement at the low peak, to calculate the difference between these two measurements and therefore estimate the amplitude of the LSM signal. This corresponds to the example of FIG. 2*c*.

It will be appreciated that other applications and embodiments may be considered.

Figure 3:
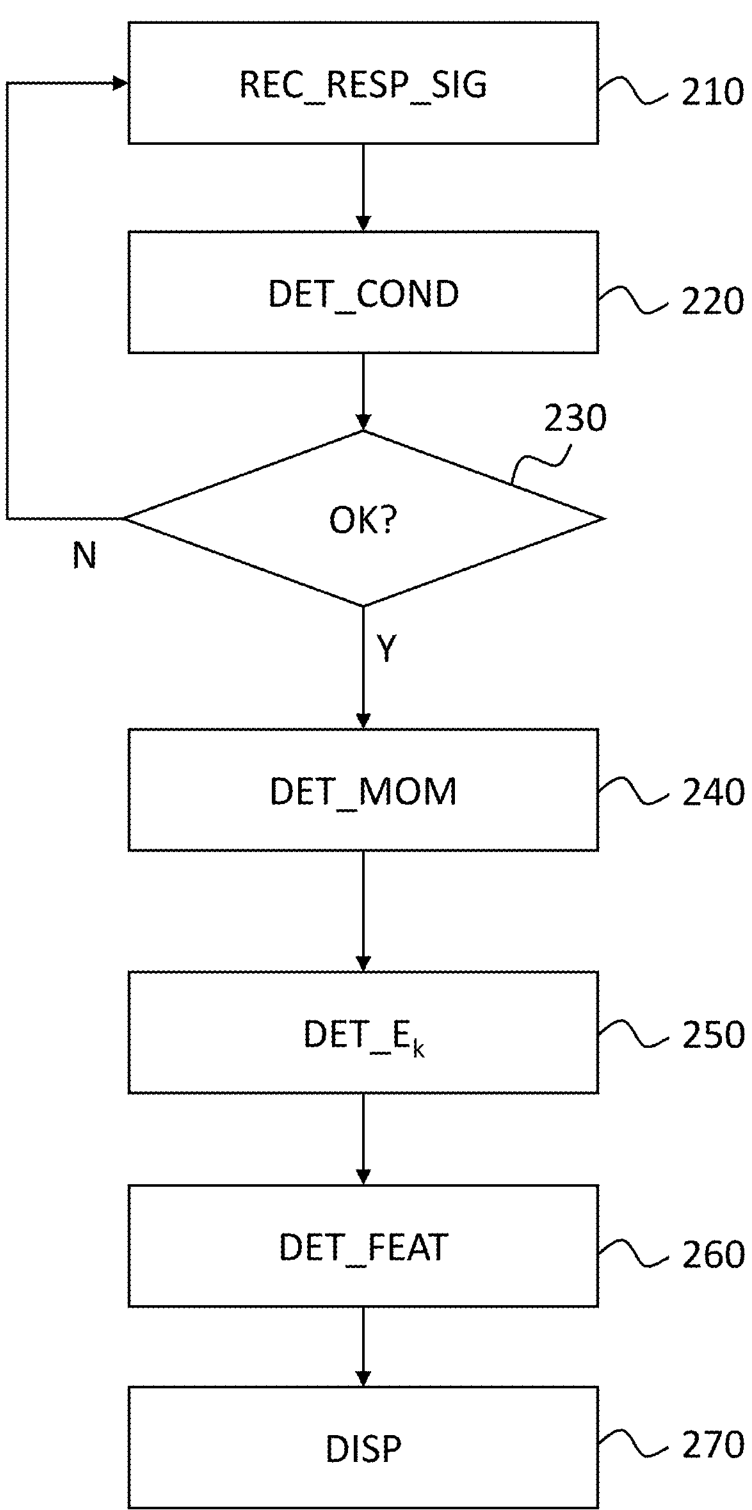
FIG. 3 is a flow-chart describing a method for measuring a mechanical property of a region of the body of a subject according to an embodiment of the invention.

FIG. 3 represents a flow-chart of a method for determining measurements of a mechanical property of a part of the liver of the spleen of the subject in one embodiment of the invention. The method of FIG. 3 may be implemented by an electronic unit of an elastography device, or by an electronic unit of a computing device external to an elastography device and configured to receive data from the elastography device. The electronic unit may include one or more electronic circuitries to carry out its function(s). The one or more electronic circuitries may include a processor (e.g. a microprocessor) and a memory coded with instructions for performing the functions of the electronic unit when the instructions are executed by the processor. In an embodiment, the electronic unit may be configured to carry out the method shown in FIG. 3.

According to the embodiment of FIG. 3, a plurality of measurements of the mechanical property are determined at specific moments of the respiratory cycles. The determined measurements are then used for determining a feature related to the mechanical property.

In the following, the mechanical property corresponds to the tissue stiffness, and more specifically a liver stiffness. It will be appreciated that any other mechanical property may be measured, for instance the elasticity, the Young's modulus, the shear modulus, the shear wave speed, the viscoelasticity, the viscosity or any composite biomarker deriving from (or combining) one or more of the previous physical quantities. Also, it will be appreciated that the invention may also be applied to the spleen.

A respiratory signal of the subject is obtained at step 210.

The respiratory signal may be acquired, for example, by a respiratory belt or a respiratory sensor, or any other technique making it possible to detect specific moments in the respiratory cycle of the subject. In an embodiment, the respiratory signal is supplied to the electronic unit of the elastography device or a remote device in communication with the elastography device.

At an optional step 220, one or more conditions for the electronic unit to enter a measurement mode may be determined. Such measurement mode may correspond to a mode in which the electronic unit is ready to start the determination of the measurements. While the electronic unit is not in the measurement mode, no measurements is taken.

The one or more conditions may include, for example:

- a condition as to whether the position and direction of probe is adequate, i.e. whether probe is correctly positioned with respect to region of body for which measurements of the mechanical property are to be obtained. The U.S. patent application Ser. No. 17/695,053 assigned to the applicant details examples of determination of such condition; and/or
- a condition as to whether tip of the probe is properly applied against body of the subject.

In an optional step 230, the electronic unit may determine whether all conditions of step 220 are met or satisfied. While at least one condition is not met or satisfied (step 220, arrow "N"), the electronic unit does not enter the measurement mode and acquisition of the measurements $E_k$ cannot begin. If all conditions are met or satisfied (step 220, arrow "Y"), the electronic unit proceeds with the measurement mode. Once the electronic unit is in measurement mode, it may monitor the occurrence of an event related to the ECG signal.

At step 240, a specific moment or instant or time of the respiratory cycle in the respiratory signal is detected by the electronic unit. As detailed above, the specific moment may correspond to an upward peak or a downward peak in the respiratory signal. The detection 240 of the moment causes, by the electronic unit, the acquisition (step 250) of a respective measurement $E_k$ of the mechanical property. As detailed above, depending on embodiments, there can be one measurement per respiratory cycle or several measurements per respiratory cycle. It is understood it is not mandatory to acquire measurements for each respiratory cycle. During certain cycles, it is possible that no measurement is acquired. The at least one measurement $E_k$ may be determined (step 250) by any elastography technique.

At step 260, at least one feature representative of the mechanical property of the subject may be determined, by the electronic unit 10, from the measurements obtained at step 250.

The feature representative of the mechanical property may be a single value determined from the obtained measurements. For example, the feature may be a function of the minimum, the maximum, a given percentile, the mean, the standard variation or any statistical indicator of the obtained measurements. The feature may also be a function of a combination of at least two statistical indicators.

In embodiments, the feature representative of the mechanical property may be determined, by the electronic unit 10, from the obtained measurements and from additional values, for example from at least one value obtained from the respiratory signal. For example, the feature may be determined from the obtained measurements and the values of the respiratory signal at times at which the measurements have been acquired. In particular, the feature may be a function of the minimum, the maximum, a given percentile, the mean, the standard variation or any statistical indicator of values derived from the measurements of the mechanical property and the values of the respiratory signal.

As mentioned above, such feature may provide more accurate information related to the mechanical property than conventional methods. In current elastography techniques, several (e.g. 10) measurements of the stiffness are determined at respective instants that can correspond to very different moments of the respiratory cycles and therefore to very different values of the stiffness. From these measurements, a feature representative of stiffness is computed (e.g. the mean or the median of the measurements), without taking into account such variability. By considering, for example, measurements always taken at the same moment (at least approximately) of the respiratory cycle, this variability is therefore reduced.

When several measurements are acquired per respiratory cycles, intermediate values can be computed from these measurements, one intermediate value corresponding to one respiratory cycle. For example, when two values are acquired at a low peak and a high peak of a same respiratory cycle, the intermediate value may be the absolute value of the difference between the two measurements. The feature may be a single value determined from the obtained intermediate values. For example, the feature may be a function of the minimum, the maximum, a given percentile, the mean, the standard variation or any statistical indicator of the obtained intermediate values. The feature may also be a function of a combination of at least two statistical indicators.

At an optional step 270, the feature determined at step 260 can be displayed on a screen of the elastography device and/or a device in communication with the elastography device, to be used by the medical practitioner. Other information may be displayed, in alternative or in addition. For example, the signal respiratory signal may be displayed, as well as an elastogram.

It will be appreciated that the measurements of the mechanical property of step 250 may be obtained by using any elastography technique. In particular, the measurements of the mechanical property may be acquired by an elastography device using a Vibration-Controlled Transient Elastography (VCTE) technology, such as the device described in FIG. 4. It should be noted, however, that the present invention is not limited to such technology.

Figure 4:
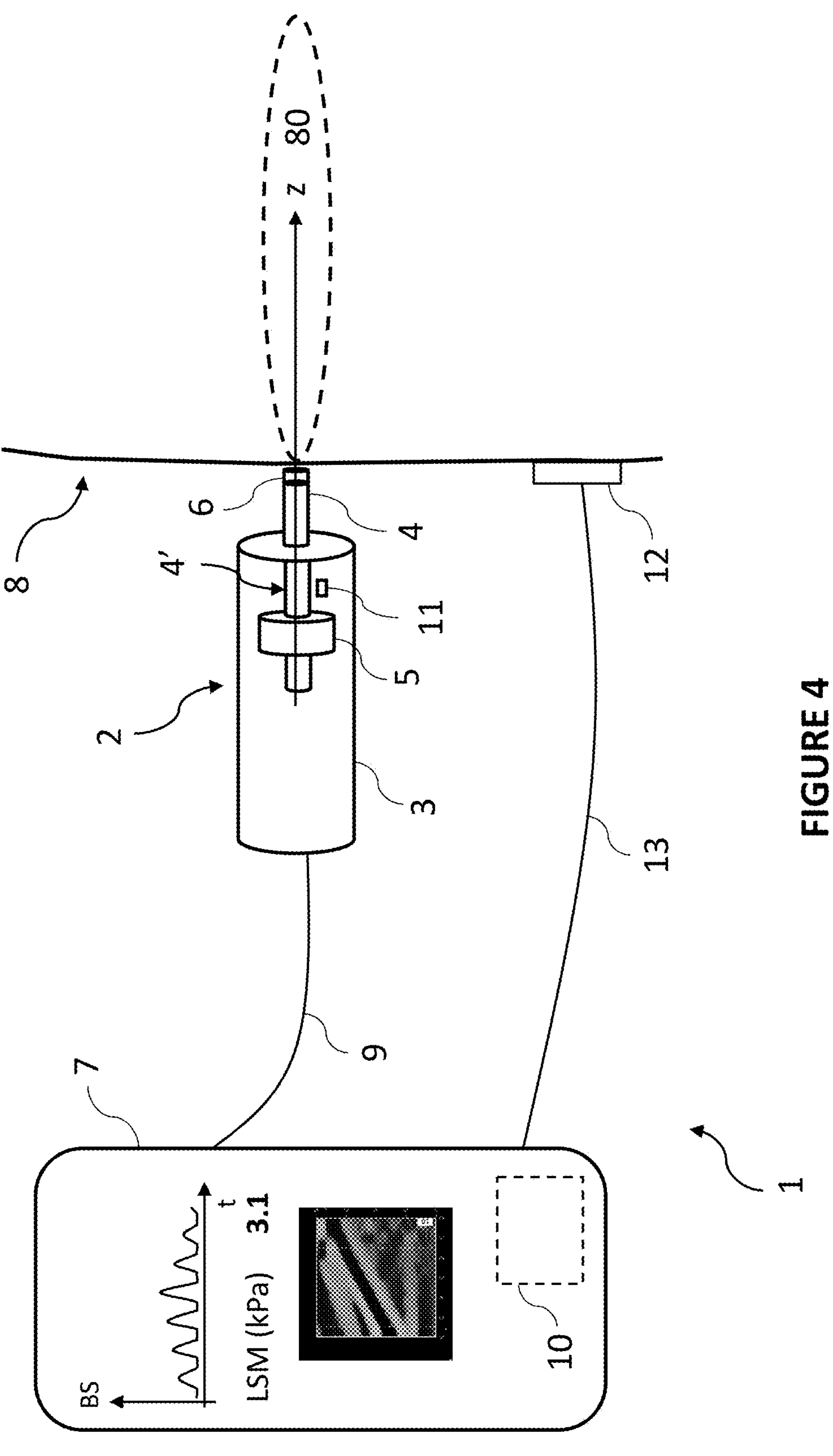
FIG. 4 schematically represents an example of an elastography device according to one or more embodiments of the invention.

The elastography device 1 of FIG. 4 comprises a probe 2 including a probe casing 3 (which forms the main body of the probe) to be handheld and a protruding part, which protrudes from the casing 3. The protruding part can be applied against the body 8 of the subject, to deliver mechanical pulses to it, and to transmit and acquire ultrasound (U/S) shots.

In the example of FIG. 4, the protruding part is a tip 4, for instance a cylindrical tip (with a circular transducer 6 at its end).

Still, in other embodiments, the protruding part could be an ultrasound head (located at an end of the probe) including an array, for instance a linear array of U/S transducers. In this regard, it may be noted that the proposed technique can be used with a single element ultrasound transducer or with a multi-element ultrasound transducer (like an array of U/S transducers, for example a linear or convex or phased array ultrasound probe). While a single element ultrasound transducer is adapted to display A-mode and M-mode ultrasound imaging, a multi element ultrasound transducer can also display a B-mode image allowing an easier localization of the to-be-measured tissue. In the case of a multi element ultrasound transducer, at least one of the beamformed ultrasound lines is used to track how the mechanical pulses propagate. To this end, using the center beamformed ultrasound line (which is aligned with the probe axis) is beneficial, for symmetry considerations.

The probe 2 comprises also a low frequency vibrator 5, and the U/S transducer 6, which is fixed at an end of a tip 4. Here, the U/S transducer 6 plays both the role of an ultrasound emitter and the role of an ultrasound receiver (alternatively). Still, in other embodiments, the probe may comprise an U/S emitter and an U/S receiver distinct from each other. Here, the U/S transducer 6 is arranged on the axis z of the vibrator. Still, in other embodiments, the U/S transducer could be located elsewhere on the probe, not necessarily on the vibrator's axis.

The tip 4 is actuated by the low frequency vibrator 5. Here, the vibrator 5 is arranged to move the tip 4 relative to the probe casing 3. The vibrator 5 is arranged to move a shaft 4', the end of which forms the tip 4 of the probe. Still, in other embodiments, the probe may be an inertial probe. In such an inertial probe, the tip, or more generally the protruding part of the probe, could be bound to the probe casing with no motion with respect to the probe casing, the vibrator being then arranged to move a mass, inside the casing, to make the whole probe moving towards the tissue and back (by virtue of a recoil effect).

The vibrator 5 is a low frequency vibrator in that it moves the tip with a central, average frequency smaller than 500 hertz, or even smaller than 100 hertz (in contrast with ultrasound shots or echo signals, whose central frequency is typically higher than 1 megahertz, for instance between 1 and 5 megahertz). The vibrator is a low-frequency electromechanical actuator, for instance with one or several coils and magnets, like a loud-speaker actuator.

In this device 1, the vibrator 5 is rotationally symmetrical around a vibrator axis, which coincides with the probe axis z. When the vibrator 5 vibrates, it induces displacements that are mainly longitudinal, parallel to its axis. The shaft 4' is centered onto the axis z, and the vibrator 5 is arranged to move this shaft along the axis z.

In practice, the displacement of the ultrasound transducer 6, induced by the vibrator 5, has a peak-to-peak amplitude between 0.2 mm and 10.0 mm, and, in an embodiment, between 0.5 and 3.0 mm.

The probe 2 comprises a displacement sensor 11, arranged to output a measurement signal Sd representative of the displacement of the ultrasound transducer 6. In this embodiment, the measurement signal Sd is representative of the displacement of the ultrasound transducer 6 relative to the probe casing 3. A part of the displacement sensor 11 is fixed on the shaft 4' mentioned above while another part of the sensor is fitted in the probe, with no motion with respect to the casing 3. The displacement sensor 11 may be a Hall-effect sensor, an induction displacement sensor, or any other suitable sensor.

In one or several embodiments, the device 1 may further comprise at least one respiratory sensor 12 to be placed on the body of the subject (in the case of a chest pressure sensor for example) or near the body of the subject (in the case of a breathing sensor using a microphone or an air sensor for example—such a sensor can typically be placed near the mouth and/or nose of the subject) to record the respiratory activity of the subject and obtain a respiratory signal of the subject.

It is noted that, alternatively, the respiratory sensor 12 may not be part of the device 1, but may be connected to the device 1, for example via one or several wires, so that the device 1 may receive a signal related to respiratory activity of the subject. The device 1 may, for example, receive data acquired by the sensor and process these data to obtain the respiratory signal, or, alternatively, directly receive the respiratory signal of the subject.

The probe 2 is operatively connected to a central unit 7, which has the structure of a computer (e.g. a laptop, a smartphone, or a dedicated electronic device arranged to control and to interface the probe, and to process the signals acquired). The central unit 7 comprises at least a memory and a processor. The at least one memory is coded with machine readable instructions for carrying out function(s) of the central unit 7 when executed by the processor. The central unit 7 may also comprise a display and a graphical user interface for displaying some pieces of information, such as the curve representing the signal representative of the variations of the mechanical property of the region 80 over time during an examination of the subject, one or several elastograms, one or more features related to the mechanical property (e.g. the baseline/resting value or the dynamic value), or other pieces of information (e.g. the LSM signal). The display and graphical user interface may be controlled by the processing circuit of the central unit 7 to cause the graphical user interface to display visual information to the operator or prompt the operator of the elastography device 1 to initiate one or more actions or commands. For example, the graphical user interface may be controlled by the central unit 7 to prompt the operator of the elastography device 1 to initiate or start an elastography measurement of a mechanical property of an organ of the patient (e.g. a liver stiffness measurement or a spleen stiffness measurement) in association with the respiratory signal obtained with the respiratory sensor 12. In one or more embodiments, the processing circuit of the central unit 7 may cause the graphical user interface to display a menu that enables the operator to select and carry out specific types of measurements, such as, for example, a measurement of the mechanical property that is determined with or without the respiratory signal, and/or a measurement of the resting and/or dynamic component(s) or value(s) related to the mechanical property to provide different types of diagnostic. The processing circuit of the central unit 7 may cause the graphical user interface to display the measurement results, such as the measurement of the mechanical property that is determined with or without the respiratory signal, and/or a measurement of the resting and/or dynamic component(s) or value(s) related to the mechanical property. The central unit 7 comprises also at least one user interface, such as a keyboard, a mouse, one or more buttons and/or a touch screen to enter one or more data and/or information and/or parameters. As a non-limiting example, the additional parameters may include the age, height, weight, body mass index (BMI), fat mass index of the patient or subject.

The probe may be connected to the central unit 7 by a connection cable 9, or by a wireless link. Similarly, the respiratory sensor may be connected to the central unit 7 by a connection cable 13 or by a wireless link (e.g. via WiFi or BLUETOOTH® (a short-range wireless technology standard).

The central unit 7 may also comprise an electronic unit 10 connected to the vibrator 5, the U/S transducer 6 and the respiratory sensor 12 and configured (for instance, programmed via instruction stored in a memory) to control elastography device 1 so that it acquires (or "determines") a plurality of measurements of the mechanical property of the region 80 of the body, to receive and process data obtained from the respiratory sensor 12 and to implement the method of FIG. 3. The electronic unit 10 may receive the signal acquired by the respiratory sensor 12.

In one or more embodiments, the plurality of measurements of the mechanical property may be acquired in response to a manual triggering by the operator. This manual triggering may be achieved by actuating a push-button switch arranged on the probe casing 3, or by actuating a footswitch, for instance.

Figure 5:
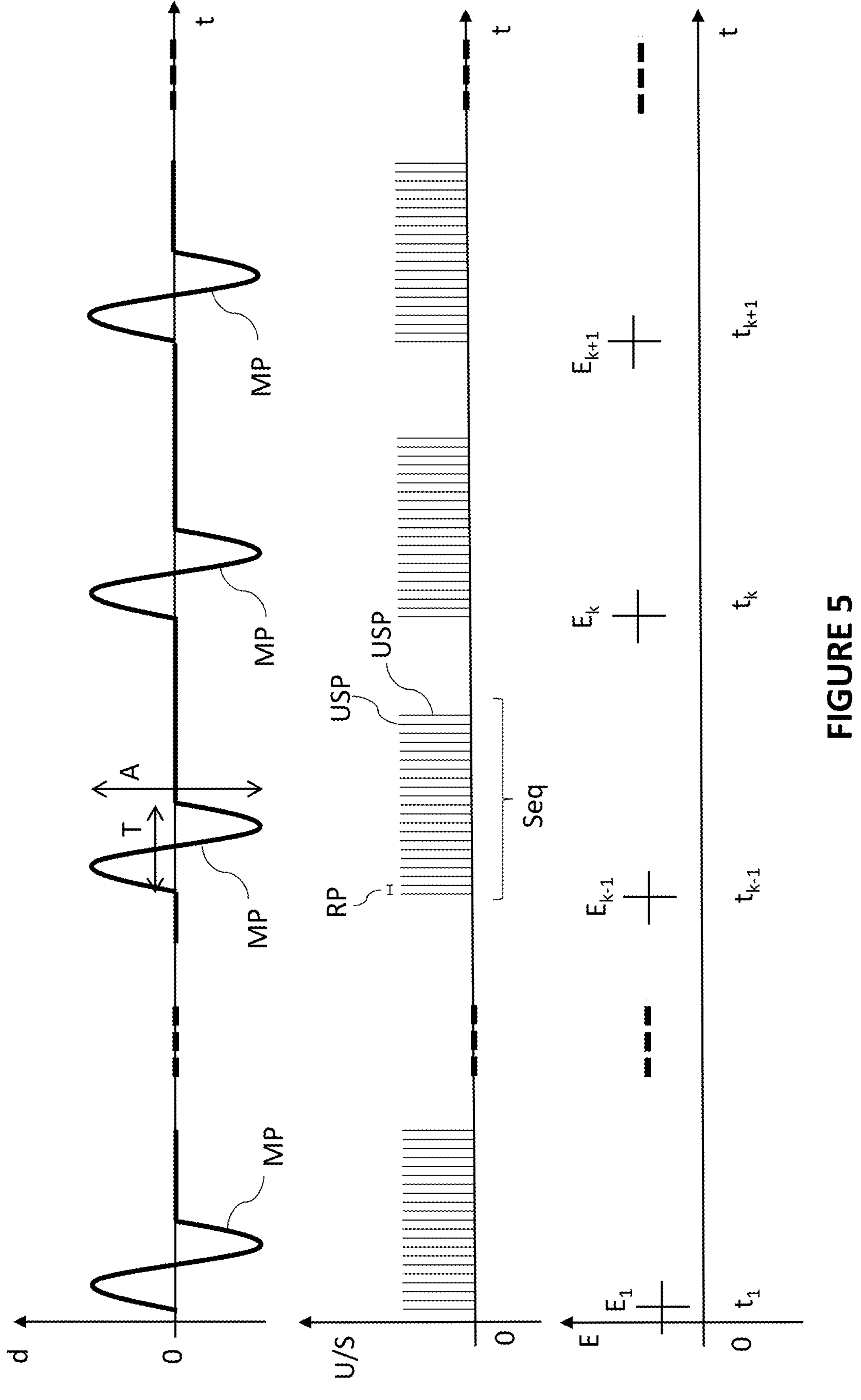
FIG. 5 represents a sequence of mechanical and ultrasound pulses emitted by the elastography device of FIG. 4 according to one or more embodiments of the invention.

As represented in FIG. 5, to obtain measurements of the mechanical property, the electronic unit 10 may be configured to control the low frequency vibrator 5 to deliver to the body 8 of the subject a plurality of mechanical pulses MP, each pulse MP being a transient, low frequency mechanical pulse. Each mechanical pulse MP corresponds to a transient displacement d of the shaft 4' along the axis z directed towards the subject's body (see FIG. 4). The displacement d of the shaft 4' induced by the vibrator may for instance correspond to one period of a sinusoid having a duration T between 5 ms and 50 ms (i.e. a frequency between 20 Hz and 200 Hz).

The displacement d of the shaft 4', induced by the vibrator 5, has a peak-to-peak amplitude A between 0.2 mm and 10.0 mm, and in an embodiment between 0.5 and 3.0 mm.

The central frequency of each mechanical pulse MP may be between 10 Hz and 500 Hz, for example between 50 Hz and 200 Hz when the elastography device is configured to characterize the liver of patients (typically 50 Hz in this case).

As represented in FIG. 5, for each mechanical pulse MP, the electronic unit 10 controls the U/S (ultrasound) transducer 6 (with the U/S pulser 41 of the U/S front end 40, among others) so that the U/S transducer 6 emits a sequence Seq of ultrasound pulses USP, and acquires echo signals received in response by the U/S transducer 6, to track how the mechanical pulse MP propagates through the probed region 80 of the body 8 of the subject, located in front of the tip 4 of the probe.

For this sequence Seq, the central frequency of each ultrasound pulse USP is comprised for instance between 0.5 and 10.0 megahertz. The ultrasound pulses of the sequence Seq may be transmitted one at a time, two successive pulses being separated by a pulse repetition period RP, this pulse repetition period being typically between 0.1 millisecond and 2 milliseconds (which corresponds to a pulse repetition frequency between 0.5 kilohertz and 10 kilohertz), and in an embodiment between 0.3 ms and 1 ms. The ultrasound pulses USP of the sequence Seq mentioned above may also be transmitted by groups, for instance by groups of two pulses (to compute correlations between the two corresponding echo signals). The two pulses of each group may be separated by duration between 50 and 200 microseconds, while the groups of pulses themselves are separated by a longer duration, for instance higher than 0.2 or 0.5 ms. It will be appreciated that other transmission sequences can also be considered in various embodiments.

The total duration of the sequence of U/S pulses Seq may be between 25 ms and 200 ms. This duration may be selected depending on the shear wave frequency and depending on the speed of propagation of the elastic wave which is the slower and depending on the depth of the region to be observed. For instance, for a shear wave frequency of 50 Hz, an 80 mm depth and a speed of propagation of 1 m/s (typical for shear waves in the liver of a subject), the sequence may have a duration of 100 ms.

Regarding the echo signals, acquired to track the propagation of the mechanical pulse considered, each of them is formed by a signal, received over time t by the U/S transducer 6 after the emission of one of the U/S pulses USP. It is more precisely the signal received within a given temporal window starting after this emission and having a given duration.

In the embodiments described herein, for each mechanical pulse MP, the electronic unit 10 determines tissue strain data, representative of tissue strain within the region 80, as a function of time t and as a function of depth z within the region 80. The tissue strain data is determined from the echo signals acquired to track how the mechanical pulse MP propagates through the region 80. When represented graphically as a function of time and depth, such tissue strain data forms an elastogram, from which a measurement of the mechanical property (e.g. the tissue stiffness) may be determined.

The tissue strain data is determined, from the echo signals, using a correlation technique or another patterning matching algorithm, to determine how portions of the tissue move under the influence of the elastic wave that is passing through it (the elastic wave being generated by the periodic mechanical vibration delivered by the system). For instance, for each couple of two successively received echo signals, the two echo signals are correlated with each other, which enables one to determine tissue displacement (namely, the tissue displacement that occurred between the two U/S pulses), as a function of depth, and at given time.

As mentioned above, for each mechanical pulse MP, or at least for several of them, respective tissue strain data may be obtained and a respective measurement ($E_1$, $E_{k-1}$, $E_k$, $E_{k+1}$ in FIG. 5) of the mechanical property of the region 80 may be determined. Each determined measurement $E_n$ may be associated with a respective time $t_n$ which represents the instant at which the measurement is performed. For example, as in the embodiment represented in FIG. 5, each measurement $E_n$ is associated with a respective time $t_n$ equal to the time at which the corresponding mechanical pulse MP has been emitted. Other embodiments are possible. For example, each measurement $E_n$ may be associated with a respective time $t_n$ equal to the time at which the last of the echo signals is acquired in response to the emission of the corresponding sequence Seq of U/S pulses USP. Alternatively, each measurement $E_n$ may be associated with a respective time $t_n$ equal to the time at which the measurement $E_n$ is determined (i.e. after the determination of the corresponding tissue strain data). It is noted that the values of the times $t_n$ obtained by all these embodiments differ very little from each other, and that this difference has little impact on the interpretation of the signal E (t) obtained.

The mechanical property of the tissue, related to low frequency shear wave propagation may be a quantity related to the tissue stiffness, such as the propagation speed of shear waves $V_s$, the shear modulus of the tissue or the Young's modulus E of the tissue (which can be derived from the slope of the stripes identified in the elastogram, or from the variation of the time of flight of the measurement pulse as a function of depth). It may also be a quantity related to low frequency shear wave attenuation in the tissue, like viscosity.

As mentioned above, it is noted that, even the elastography device represented in FIG. 4 is a VCTE device, aspects of the present invention can be generalized to any type of elastography device. In particular, the present invention may be applied to other TE (Transient Elastography) devices, for example devices implementing ARFI (Acoustic Radiation Force Impulse) or SWE (Shear Wave Elastography) technologies. In ARFI and SWE, unlike in the VCTE technology, a longitudinally moving shear wave is not generated by an external vibrator. Instead, in ARFI, pressure radiation generated by ultrasounds is focused in a region of interest. The radiation pressure generates a laterally moving shear wave that is tracked outside the region of interest using ultrasound tracking pulses.

It is noted that, in the embodiments described above with reference to FIGS. 2*a* and 2*b*, there is no constraint as to the speed of acquisition of measurements by the elastography device. Indeed, the measurements are acquired at specific moments of the respiratory cycle, at a frequency of at most one measurement per respiratory cycle (it being understood that it is possible not to acquire measurements at certain cycles).

In the embodiments described above with reference to FIG. 2*c*, the elastography device is able to acquire at least two measurements per respiratory cycle (even if this constraint can be lifted, for example, by considering a pair of values including the value at the end of inspiration of a respiratory cycle and the value at the end of expiration of the following respiratory cycle). Knowing that the average duration of the respiratory cycle of an adult is around 3 seconds, this means that the elastography device is configured to acquire one measurement each 1.5 s.

It will be appreciated that for all embodiments, the elastography device can be configured to acquire measurements at a much higher frequency, for example several measurements per second. In particular, the elastography device can be configured to acquire at least 4 measurements per second, for example 5 measurements, 10 measurements or even more than 10 measurements per second. An example of such elastography device is provided for example in patent EP 4 245 224 assigned to the applicant.

Such high acquisition rate elastography devices make it possible, for example, to obtain a signal representing variations in the measurement of the mechanical property, such as the LSM signal 101 shown in FIG. 1.

With such elastography devices, it is possible, for example, to continuously acquire measurements (i.e. to perform acquisitions at a predefined rate, for example 5 or 10 measurements per second), to obtain, from the measurements thus acquired, the signal representing the temporal variations in the measurement of the mechanical property, and to determine, from the signal obtained, measurements corresponding to specific moments of the respiratory cycle (i.e. the measurements of step 250 of FIG. 3).

Figure 6:
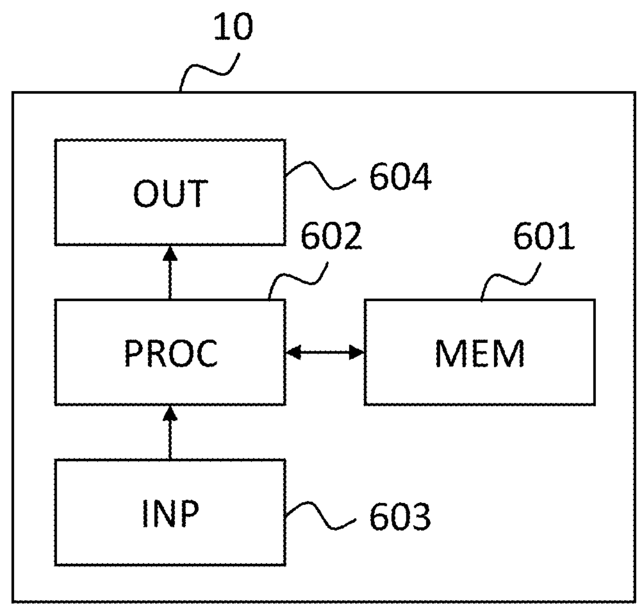
FIG. 6 schematically represents an electronic unit of an elastography device according to one or more embodiments of the invention, and FIG. 7 schematically represents an elastography system according to an embodiment of the invention.

FIG. 6 schematically represents an example of an electronic unit 10 of the elastography device 1 configured to implement the method of FIG. 3.

The electronic unit 10 can form at least part of a computer, and includes a non-transitory memory 601 to store program instructions loadable into a circuit computer 602 (e.g. a microelectronic circuit or circuitry) and adapted to cause the computer circuit 602 to carry out one or several steps of the method(s) or function(s) of the device(s) described herein when the program instructions are executed by the computer circuit 602.

The memory 601 may also store data and useful information for carrying the steps of the method(s) described herein. The circuit 602 may be for instance:

- a processor or a processing unit adapted to interpret instructions in a computer language, the processor or the processing unit may comprise, may be associated with or be attached to a memory comprising the instructions, or
- the association of a processor/processing unit and a memory, the processor or the processing unit adapted to interpret instructions in a computer language, the memory comprising the instructions, or
- an electronic card wherein the steps of the invention are described within silicon, or
- a programmable electronic chip such as a FPGA chip (for «Field-Programmable Gate Array»).

This electronic unit 10 further comprises an input interface 603 for receiving data related to LS measurements and data related to a respiratory signal and an output interface 604 for providing at least a feature determined in step 260 of FIG. 3.

Optionally, the computer circuit 602 may be connected to a screen and may be configured to control the screen and the graphical user interface to cause the graphical user interface to display predetermined information such as, for example, the curve of the respiratory signal, value of the determined feature, etc.

Figure 7:
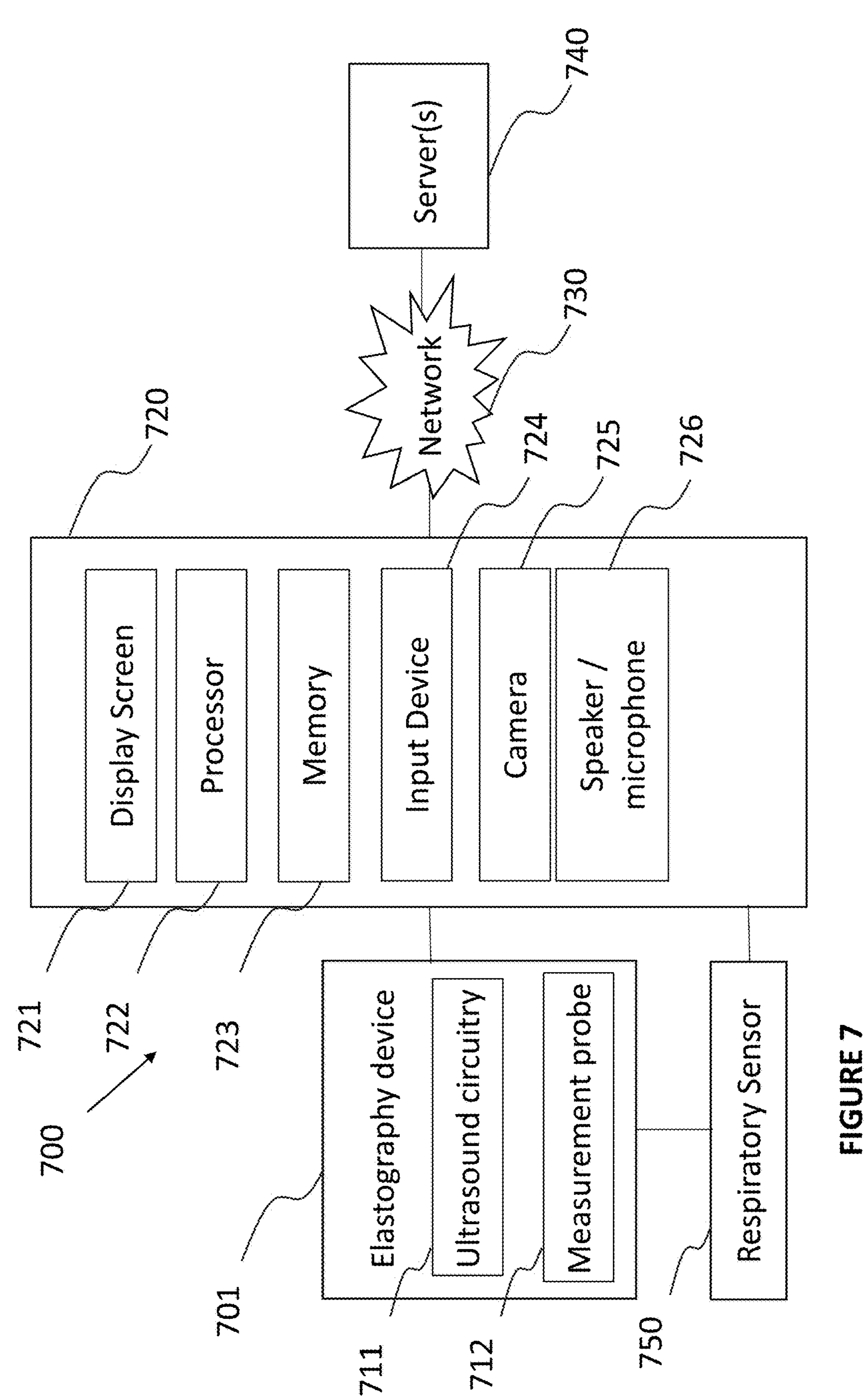

FIG. 7 illustrates a schematic block diagram of an example of an elastography system 700 upon which various aspects of the technology described herein may be practiced. The elastography system 700 includes an elastography device 701, a processing device 720, a network 730, and one or more servers 740. The elastography system may also include a respiratory sensor 750, which may be in communication with the elastography device 701, the processing device 720, or both (as shown in FIG. 7)

The elastography device 701 includes ultrasound circuitry 711 and a measurement probe 712 for carrying out ultrasound and elastography measurements. The processing device 720 may be a portable device (e.g., a phone, a tablet, a computer or a separate medical device) that includes a display screen 721 a processor 722, a memory 723, an input device 724, a camera 725 and a speaker 726. The processing device 720 is in wired (e.g., through a lightning connector or a mini-USB connector) and/or wireless communication (e.g., using BLUETOOTH® (a short-range wireless technology standard), ZIGBEE, and/or WiFi wireless protocols) with the elastography device 701. In addition, optionally, the processing device 720 is in wireless communication with the one or more servers 740 over the network 730. However, the wireless communication with the server(s) is optional. The processing device 720 may be configured to carry out one or more functions of the electronic unit 10 previously described such as, e.g., determining the resting value, the resting component and/or the dynamic component.

The elastography device 701 may be configured to generate elastography and ultrasound data that may be employed to generate an ultrasound image and an elastogram image. The elastography device 701 may be constructed in any of a variety of ways. In some embodiments, the elastography device 701 may be a vibration-controlled-transient-elastography device that is configured to perform liver stiffness measurements. An example of a vibration-controlled-transient-elastography device is shown and described in FIG. 4.

The ultrasound circuitry 711 may be configured to generate the ultrasound and elastography data. The ultrasound device 701 may transmit ultrasound data and/or ultrasound images and/or elastography data (such as, but not limited to, liver stiffness measurements) to the processing device 720 over a wired (e.g., through a lightning connector or a mini-USB connector) and/or wireless (e.g., using BLUETOOTH® (a short-range wireless technology standard), ZIGBEE, and/or WiFi wireless protocols) communication link.

Referring now to the processing device 720, the processor 722 may include specially-programmed and/or special-purpose hardware such as an application-specific integrated circuit (ASIC). For example, the processor 722 may include one or more graphics processing units (GPUs). The processing device 720 may be configured to process the ultrasound data and/or elastography data received from the elastography device 701 to generate ultrasound and/or elastogram images for display on the display screen 721. The processing device 720 may also be configured to determine the mechanical property, the resting value, the resting component and/or the dynamic component/value related to the mechanical property.

The determining of the mechanical property, the resting value, the resting component and/or the dynamic component/value related to the mechanical property may be performed by, for example, the processor 722. In one or more embodiments, the processor 722 may also be adapted to control the acquisition of ultrasound and/or elastography data with the elastography device 701. In one or more embodiments, the processor 722 may also be configured to receive the respiratory signal acquired by the respiratory sensor 750. In one or more embodiments, the processor 722 may also be adapted to control the display screen 721 via a graphical user interface and/or speaker/microphone 726 to instruct and guide the operator of the elastography device 701 to carry out specific steps of the method for determining the mechanical property, the resting value, the resting component and/or the dynamic component/value related to the mechanical property. For example, the processor 722 may be configured to control the display screen 721 to display via a graphical user interface to carry out the measurements with or without the respiratory sensor 750. Then, the processor 722 may be configured to control the display screen 721 to display via a graphical user interface a menu to select one or more options for carrying out the mechanical property, the resting value, the resting component and/or the dynamic component/value related to the mechanical property. The selection of one or more options via the graphical user interface may trigger, by the processor 722, a routine that prompts the operator of the elastography device 701 initiate or start the measurement(s). The processor 722 may also be configured to control the display screen 721 to control the graphical user interface of the display screen 721 or of the elastography device to display the resting component/value and/or the dynamic component/value.

The processing device 720 may be configured to perform certain of the processes and methods described herein using the processor 722 (e.g., one or more computer hardware processors) and one or more articles of manufacture that include non-transitory computer-readable storage media such as the memory 723. The processor 722 may control writing data to and reading data from the memory 723 in any suitable manner. To perform certain of the processes described herein, the processor 722 may execute one or more processor-executable instructions stored in one or more non-transitory computer-readable storage media (e.g., the memory 723), which may serve as non-transitory computer-readable storage media storing processor-executable instructions for execution by the processor 722. The camera 725 may be configured to detect light (e.g., visible light) to form an image. The display screen 721 may be configured to display images and/or videos, and may be, for example, a liquid crystal display (LCD), a plasma display, and/or an organic light emitting diode (OLED) display on the processing device 720. The input device 724 may include one or more devices capable of receiving input from a user and transmitting the input to the processor 722. For example, the input device 724 may include a keyboard, a mouse, a microphone, touch-enabled sensors on the display screen 721, and/or a microphone. The display screen 721, the input device 724, the camera 725, and the speaker 740 may be communicatively coupled to the processor 722 and/or under the control of the processor 722.

It should be appreciated that the processing device 720 may be implemented in any of a variety of ways. For example, the processing device 720 may be implemented as a handheld device such as a mobile smartphone or a tablet. Thereby, a user of the elastography device 701 may be able to operate the elastography device 701 with one hand and hold the processing device 720 with another hand. In other examples, the processing device 720 may be implemented as a portable device that is not a handheld device, such as a laptop. In yet other examples, the processing device 720 may be implemented as a stationary device such as a desktop computer connected to the elastography device. The processing device 720 may be connected to the network 730 over a wired connection (e.g., via an Ethernet cable) and/or a wireless connection (e.g., over a WiFi network). The processing device 720 may thereby communicate with (e.g., transmit data to) the one or more servers 740 over the network 730. In one or more embodiments, the processing device 720 may communicate the determined measurement of the mechanical property, the determined resting component/value and/or the determined dynamic component/value, to the one or more servers 740 via the network 730.

FIG. 7 should be understood to be non-limiting. For example, the elastography system 700 may include fewer or more components than shown and the processing device 720 may include fewer or more components than shown. While FIG. 7 represents an elastography system 700 in which the processing device 720 is separate from the elastography device 701, it will be appreciated that the processing device 720 can be part of (e.g. included in) the elastography device. For example, the display screen 721, the processor 722, the memory 723, the input device 724 and the speaker/microphone 726 can be elements of the elastography device 701. In this implementation, the processor 722 can be part of, or can control, or can be under the control of, the ultrasound circuitry 711 or can be controlled by a master processor of the elastography device 701.

Moreover, it will be appreciated that the processing device 720 could be in communication with more than one elastography devices so as to receive liver stiffness measurements from a plurality of elastography devices. Furthermore, it is contemplated that the first and second liver stiffness measurements could be carried out with, respectively, different elastography devices and/or with, respectively, different elastography techniques (such as VCTE and ARFI).

The articles "a" and "an" may be employed in connection with various elements and components of compositions, processes or structures described herein. This is merely for convenience and to give a general sense of the compositions, processes or structures. Such a description includes "one or at least one" of the elements or components. Moreover, as used herein, the singular articles also include a description of a plurality of elements or components, unless it is apparent from a specific context that the plural is excluded.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

Expressions such as "comprise", "include", "incorporate", "contain", "is" and "have" are to be construed in a non-exclusive manner when interpreting the description and its associated claims, namely construed to allow for other items or components which are not explicitly defined also to be present. Reference to the singular is also to be construed in be a reference to the plural and vice versa.

A person skilled in the art will readily appreciate that various parameters disclosed in the description may be modified and that various embodiments disclosed may be combined without departing from the scope of the invention. For example, various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Having described above several aspects of at least one embodiment, it is to be appreciated various alterations, modifications, and improvements will readily occur to those skilled in the art. Such alterations, modifications, and improvements are intended to be aspects of this disclosure. Accordingly, the foregoing description and drawings are by way of example only.

The invention claimed is:

1. An elastography method implemented by an elastography device including an elastography probe, the method comprising:

obtaining, using a respiratory sensor separate from the elastography probe, a respiratory signal related to a respiratory activity of a subject; and acquiring, using the elastography probe of the elastography device, a plurality of measurements of a mechanical property of a region of a body of the subject, the region being a part of a liver or a spleen of the subject;

wherein each measurement among at least a subset of the plurality of measurements of the mechanical property is acquired at a same moment of a respective respiratory cycle determined from the respiratory signal.

2. The elastography method of claim 1, wherein each measurement of the plurality of measurements of the mechanical property is acquired at a same moment of a respective respiratory cycle determined from the respiratory signal.

3. The elastography method of claim 1, wherein the plurality of measurements of the mechanical property is partitioned into a plurality of subsets of measurements, each subset of measurements comprising measurements acquired at a respective moment of the respiratory cycle, the moments of the respiratory cycle associated with different subsets of measurements being different from each other.

4. The elastography method of claim 1, further comprising, for each measurement of the plurality of measurements:

detecting an event in the respiratory signal, said event corresponding to a beginning of an inspiration, an end of an inspiration, a beginning of an expiration, or an end of an expiration, and acquiring the measurement upon the detection of the event.

5. The elastography method of claim 4, wherein each measurement of the plurality of measurements is acquired at a respective time corresponding to a time at which a cardiac signal is detected.

6. An elastography method implemented by an elastography device, the method comprising:

obtaining, using a respiratory sensor, a respiratory signal related to a respiratory activity of a subject;

acquiring, using an elastography probe of an elastography device, a plurality of measurements of a mechanical property of a region of a body of the subject, the region being a part of a liver or a spleen of the subject, and for, each measurement of the plurality of measurements, detecting an event in the respiratory signal, said event corresponding to a beginning of an inspiration, an end of an inspiration, a beginning of an expiration, or an end of an expiration, and acquiring the measurement upon the detection of the event, wherein each measurement among at least a subset of the plurality of measurements of the mechanical property is acquired at a same moment of a respective respiratory cycle determined from the respiratory signal, and wherein each measurement of the plurality of measurements is acquired at a respective time corresponding to a time at which a cardiac signal is detected delayed by a predefined temporal offset.

7. The elastography method of claim 1, further comprising: determining, from the plurality of measurements, a feature related to the mechanical property.

8. The elastography method of claim 7, wherein said feature is a function of a maximum, a minimum, a mean, a standard deviation and/or a percentile of the measurements.

9. The elastography method of claim 7, wherein the feature is a function of at least one value of the respiratory signal.

10. An elastography system comprising an elastography probe and an electronic unit including a processing circuit, the electronic unit being configured to:

receive a respiratory signal, from a respiratory sensor separate from the elastography probe, related to a respiratory activity of a subject, and acquire a plurality of measurements of a mechanical property of a region of a body of the subject, the region being a part of a liver or a spleen of the subject;

wherein each measurement among at least a subset of the plurality of measurements of the mechanical property is acquired at a same moment of a respective respiratory cycle determined from the respiratory signal.

11. The elastography system of claim 10, further comprising a respiratory device configured to acquire the respiratory signal.

12. A non-transitory computer readable storage medium, having stored thereon a computer program comprising program instructions, the computer program being loadable into a data-processing unit and adapted to cause the data-processing unit to carry out the steps of an elastography method using an elastography device including an elastography probe when the computer program is run by the data-processing device, the elastography method comprising obtaining, using a respiratory sensor separate from the elastography probe, a respiratory signal related to a respiratory activity of a subject; and acquiring, using the elastography probe of the elastography device, a plurality of measurements of a mechanical property of a region of a body of the subject, the region being a part of a liver or a spleen of the subject;

wherein each measurement among at least a subset of the plurality of measurements of the mechanical property is acquired at a same moment of a respective respiratory cycle determined from the respiratory signal.

13. The elastography method of claim 1, wherein said acquiring, using the elastography probe of the elastography device, a plurality of measurements of a mechanical property of a region of a body of the subject, comprises:

emitting, by a low-frequency vibrator of the elastography probe, a transient low frequency mechanical pulse to generate at least one low-frequency elastic wave in said region, emitting, by at least one transducer of the elastography probe, ultrasonic waves to track a propagation of said at least one low-frequency elastic wave in said region, and receiving acoustic echoes in response to emission of the ultrasonic waves.

14. The elastography method of claim 1, wherein the low-frequency vibrator has a central average frequency lower than 500 Hz.

15. An elastography method implemented by an elastography device, the method comprising:

obtaining, using a respiratory sensor, a respiratory signal related to a respiratory activity of a subject; and acquiring, using an elastography probe of an elastography device, a plurality of measurements of a mechanical property of a region of a body of the subject, the region being a part of a liver or a spleen of the subject;

wherein each measurement among at least a subset of the plurality of measurements of the mechanical property is acquired at a same moment of a respective respiratory cycle determined from the respiratory signal, and wherein the respiratory signal is received by a control unit of the elastography device, the control unit being configured to trigger the measurement among the at least a subset of the plurality of measurements upon detection of an upward peak or a downward peak in the respiratory signal.

16. The elastography method of claim 1, wherein the respiratory sensor is a respiratory belt or an air sensor.

17. The elastography system of claim 10, wherein the elastography probe comprises a low-frequency vibrator configured to emit a transient low frequency mechanical pulse to generate at least one low-frequency elastic wave in said region;

one or more transducers configured to emit ultrasonic waves to track a propagation of said at least one low-frequency elastic wave in said region and to receive acoustic echoes in response to emission of the ultrasonic waves.

18. The elastography system of claim 17, wherein the low-frequency vibrator has a central average frequency lower than 500 Hz.

19. An elastography system comprising an elastography probe and an electronic unit including a processing circuit, the electronic unit being configured to:

receive a respiratory signal, from a respiratory sensor, related to a respiratory activity of a subject, and acquire a plurality of measurements of a mechanical property of a region of a body of the subject, the region being a part of a liver or a spleen of the subject;

wherein each measurement among at least a subset of the plurality of measurements of the mechanical property is acquired at a same moment of a respective respiratory cycle determined from the respiratory signal, and wherein the elastography system further comprises a control unit configured to receive the respiratory signal, the control unit being configured to trigger the measurement among the at least a subset of the plurality of measurements upon detection of an upward peak or a downward peak in the respiratory signal.

20. The elastography system of claim 10, wherein the respiratory sensor is a respiratory belt or an air sensor.

* * * * *